United States Patent [19]
Beach et al.

[11] Patent Number: 5,850,024
[45] Date of Patent: Dec. 15, 1998

[54] REDUCTION OF ENDOGENOUS SEED PROTEIN LEVELS IN PLANTS

[75] Inventors: Larry Beach, Des Moines; Bruce Orman, Ankeny; Jeff Townsend, West Des Moines; Laurie Thomas, Des Moines, all of Iowa

[73] Assignee: Pioneer Hi-Bred International, Inc., Des Moines, Iowa

[21] Appl. No.: 724,030

[22] Filed: Sep. 23, 1996

Related U.S. Application Data

[63] Continuation of Ser. No. 521,229, Aug. 30, 1995, abandoned, which is a continuation of Ser. No. 390,398, Feb. 16, 1995, abandoned, which is a continuation of Ser. No. 222,148, Apr. 4, 1994, abandoned.

[51] Int. Cl.⁶ .............................. A01H 5/10; A01H 5/00; C07K 14/415; C12N 5/14
[52] U.S. Cl. ...................... 800/250; 500/205; 435/69.1; 435/172.3
[58] Field of Search .................................... 800/250, 205, 800/DIG. 26, DIG. 70; 435/69.1, 172.3

[56] References Cited

PUBLICATIONS

Altenbach et al 1989 Pl. Molec. Biol. 13:513–522.
Altenbach et al 1992 Pl. Molec. Biol. 18:235–245.
Guerche et al 1990 Mol. Gen Genet. 221:306–314.
Serretti et al. 1994 Crop Sci 34:207–209. (Jan.).
Saalbach et al 1994 Mol. Gen. Genet: 242:226–236. (Jan.).
Bernard et al 1986 Crop Sci 26:651.
Shaul et al 1992 The Plant Journal 2(2):203–209.
Jaynes et al 1986 Trends in Biotechnol. 4:314–320.
Wilson 1987 Clin Soybeans:Improvement, Production, and Uses; 2nd edition (Wilcox ed.) Agronomy Series No. 16, pp. 643–685.
Hymowitz 19856 Cln World Soybeam Research Conference III: Proceedings (Shikles ed.) Westview Press pp. 368–373.
Richard et al 1986 J of Bacteriology 166:297–300.

*Primary Examiner*—Elizabeth C. Kemmerer
*Attorney, Agent, or Firm*—Pioneer Hi-Bred International, Inc.

[57] ABSTRACT

A plant seed and method of producing the same, genetically modified to express a preselected protein, the expression of which reduces the level of an endogenous protein in the seed. In particular, expression of a sulfur-rich, seed storage protein reduces the level of protease inhibitors in seeds.

15 Claims, No Drawings

REDUCTION OF ENDOGENOUS SEED PROTEIN LEVELS IN PLANTS

This application is a continuation of application U.S. Ser. No. 08/521 229 filed Aug. 30, 1995 now abandoned, which is a continuation of application U.S. Ser. No. 08/390,398 filed Feb. 16, 1995 now abandoned, which is a continuation of application U.S. Ser. No. 08/222,148 filed Apr. 4, 1994 now abandoned.

FIELD OF THE INVENTION

The present invention relates to the reduction of endogenous seed protein levels in plants.

BACKGROUND OF THE INVENTION

The seeds of land plants contain large quantities of storage, or reserve, proteins which are synthesized during the development of the seeds. During germination and early seedling growth, these reserves are hydrolyzed to produce metabolic intermediates for use by the growing seedling. In harvested seeds, storage proteins represent an available package of condensed food and enzymes. The food value of these seeds furthermore, could be increased by altering the composition of the reserve proteins to decrease the amount of undesirable proteins in the seeds.

It is known that mineral nutrition can have an influence on the composition of seed proteins. Chandler, et al. (1983) *Plant Physiol.* 71, 47–54; and Randall, et al (1979) *Aust. J. Plant Physiol.* 6, 11–24. Because amino acids in plants are the direct products of specific biosynthetic pathways and are required for the formation of polypeptides or plant proteins, the supply of certain minerals can alter the amount of particular amino acids available for polypeptide synthesis and, consequently, the relative proportions of proteins in the seed. Gengenbach, et al., *Genetic Manipulation of Corn Kernel Amino Acid Composition* (Jun. 20–21, 1990) Corn Utilization Conference II Proceedings, Nat'l Corn Growers Association; Chandler, et al. (1984) 75, 651–657.

Recombinant DNA and gene transfer technologies have been applied to alter enzyme activity catalyzing key steps in the amino acid biosynthetic pathway. Naito, et al, (1994) *Plant Physiol.* 104, 497–503; Glassman, U.S. Pat. No. 5,258,300; Falco, S. C. (1993) PCT Patent Appl. WO 93/19190; Galili, et al (1992) Eur. Patent Appl. EP No. 485970. However, modification of the amino acid levels in seeds is not always correlated with changes in the level of proteins that incorporate those amino acids. Burrow, et al (1993) *Mol. Gen. Genet.* 241, 431–439.

Gene modification techniques are also being used to increase or decrease the expression of endogenous proteins. However, these techniques have concentrated on direct modification of the DNA encoding the protein, or the introduction of several copies of sequences homologous to the DNA (Jorgensen, U.S. Pat. Nos. 5,034,323 and No. 5,283,184), or introduction of antisense polynucleotides. Inouye, U.S. Pat. No. 5,190,931. Until now, transformation technology has not used expression of one desirable protein to target the reduction of expression of an undesirable native protein in plants.

Some of the seed storage proteins in most, if not all, plants are in a class called protease inhibitors. These inhibitors are thought to function not only as storage proteins, but as regulators of endogenous proteases, and as proteins that protect plants from insect and pathogen attack. Liener and Kakade (1980) Protease Inhibitors. In *Toxic Constituents of Plant Foodstuffs,* 2nd ed.; Linear, I.E., Ed.; Acad. Press: New York, pp 7–71.; Ryan, Calif. (1990) *Ann. Rev. Phytopathol.* 28, 425–449.

The plant protease inhibitors are generally low molecular weight proteins, and share in common the ability to combine with particular animal, and occasionally plant proteases, thereby abolishing the activity of these enzymes. Wilson, KA. (1988) *CRC Rev. Biotech.,* 8(3), 197–216. Inhibitors that are active towards the mammalian enzymes trypsin or chymotrypsin have been best studied. This work suggests that active protease inhibitors may be toxic to humans and other animals, adversely affecting the nutritional quality of plant foodstuffs, even though they may be beneficial under other circumstances. Thus, there is a desire to minimize the amount of protease inhibitors in foods.

Protease inhibitors are particularly abundant in the legume family and constitute about 6% of the proteins of soybeans. Brandon, U.S. Pat. No. 4,959,310. Their antinutritional nature leads to pancreatic hyperplasia, acinar adenoma, and overall growth reduction when raw soybean meal is fed to monogastric animals, such as chicks, rats, and quail. Chernick, et al. (1948); Am. J. Physiol., 155, 33–41; Gumbmann, et al. (1986) p. 33–80, In *Nutritional and Toxilogical Significance of Enzyme Inhibitors in Foods.* M. Friedman (ed.), Plenum Press, New York.

Soybean (Glycine max) seed proteins are one example of storage proteins that are widely used in human foods such as infant formulas, tofu, soy protein isolates, soy flour, textured soy fibers, and soy sauce. Soybean protein products serve as an excellent source of low cost, high quality protein for human needs. Soybeans are also widely used as a component of animal feeds. However, they must be properly processed to remove or deactivate protease inhibitors.

Soybean protease inhibitors are categorized into three classes: Kunitz trypsin inhibitors, Bowman-Birk inhibitors, and glycine-rich soybean trypsin inhibitors (GRSTI). The primary structure of these inhibitors consists partly of sulfur-containing (methionine and cysteine) amino acids. Kollipara, K. P. and Hymowitz, T. (1992) *J. Agr. Food,* 40, 2356–2363.

The major and predominantly expressed form of Kunitz trypsin inhibitors (KTI) is a 21.5-kDa protein which has an inhibition specificity for trypsin. Bowman-Birk inhibitor (BBI) is a low molecular weight (8000 kDa) protein that inhibits both trypsin and chymotrypsin simultaneously at independent reactive sites. At least ten different isoforms of BBI have been reported. GRSTI are minor inhibitors of trypsin in soybean seed.

Various approaches have been taken to reduce the protease inhibitor content and/or activity of soybeans. These include physical (heat) and chemical treatment of soy products, as well as genetic alteration of soybeans through conventional breeding techniques. Liener and Kakade, supra.

In any heat treatment, care must be taken because, even though heating is required to destroy the trypsin inhibitors, improper heating will result in damage to the protein product itself. Furthermore, although the protease inhibitor activity is largely inactivated by denaturation through conventionally applied heat treatment of soy flour, 10–15% residual activity usually remains. The unusual structure of the BBI is the most likely reason for this residual activity. BBI is strongly cross-linked by disulfide bonds which gives the molecule resistance to heat denaturation. Thus, heat treatment of seed or soy products to reduce inhibitor expression is not completely successful and furthermore, is costly in energy usage.

The solvent-extraction method is another process used to eliminate protease inhibitors from raw soybeans. This chemical extraction, while removing the various inhibiting materials however, results in considerable loss of the oil in the seed, thus reducing its food value. At the same time, the solvent poses problems of cleanup and disposal.

Genetic modification of the soybean plant to develop low inhibitor activity varieties has also been proposed but has inherent limitations. Desirable nutritional value may be lost concomitant with the reduction of the inhibitors, and cross pollination of the genetic variant with another cultivar could result in reexpression of the protease inhibitor gene. Further, altering expression of one inhibitor may not affect the expression of another. As yet, conventional breeding and tissue culture technology has been unable to produce a soybean plant with low levels of protease inhibitors although a need exists for such plants.

Until now, no method existed to reduce the level of all protease inhibitors in plant seeds. In fact, no method existed to purposely use expression of one protein to reduce the level of another protein through limitation of an amino acid source.

However, we have observed that as a result of expression of a particular protein during the development of seeds, other storage proteins can be reduced in quantity. Specifically, we have concentrated on the reduction of antinutritional proteins through the expression of another preselected protein in soybean that contains sulfur amino acids. Our results indicate that undesirable antinutritional proteins such as protease inhibitors may be successfully reduced by expressing other, more desirable proteins containing amino acids that are common and essential to both the antinutritional protein and the preselected protein.

While not intending to be limited in theory, it is thought that this method of reducing antinutritional proteins works because the pool of the available amino acids common to both proteins is limited during development of the seeds. Therefore, reducing the source of the amino acid through increased synthesis of the preselected protein inhibits synthesis of the antinutritional protein.

Therefore, it is an object of this invention to provide a novel method to eliminate or reduce the content of endogenous proteins in plant seeds.

It is another object of this invention to provide plant seeds that have a reduced content of an endogenous protein as a result of increasing the content of a preselected protein with enhanced nutritional value.

It is another object of this invention to provide plant seeds that require no time-consuming or costly processing to eliminate protease inhibitor activity.

Still another object of this invention is to provide a novel method to eliminate or reduce antinutritional proteins from soybeans while retaining and even increasing the content of nutritional proteins in soybean seeds.

Yet another object of this invention is to reduce endogenous proteins in seeds by reducing the available amino acids required to synthesize the endogenous proteins.

A still further object of the present invention is to produce soybean seeds with reduced or eliminated protease inhibitor content by reducing the available sulfur-containing amino acids required to synthesize the protease inhibitor by expressing a preselected sulfur-containing protein.

A further object of this invention is to provide a transgenic plant that produces a seed having little or no protease inhibitor content.

SUMMARY OF THE INVENTION

In accordance with these objectives, the present invention provides a plant seed that is genetically modified, relative to a wild type of the species of the seed, to preferentially express a preselected protein, whereby the content of a second, endogenous protein is diminished in the seed. The preselected protein in the plant seed can be a second endogenous protein which the seed is genetically modified to overexpress or it can be a heterologous protein. Examples of preselected proteins can be, but are not limited to, a methionine-containing protein, a cysteine-containing protein, a lysine-containing protein, a glycine-rich protein, a tryptophan-containing protein, or a tyrosine-containing protein.

The invention is based on the discovery that, during development, when the plant seed has a finite amount of an amino acid required for synthesis of the antinutritional protein, increased expression of another protein requiring the same amino acid, will result in reduction or elimination of the final content of antinutritional protein in the seed, thus eliminating or reducing the need to further process the seed-based foodstuffs to effect a reduction in content.

Therefore, the present invention provides a plant seed with reduced sulfur-containing, antinutritional proteins resulting from the reduction of sulfur-containing amino acids in developing seeds. The sulfur amino acid pools in developing seeds are redistributed by expressing a sulfur-containing protein in the developing seeds. Further, the preselected protein can be a desirable source of the amino acid in question, thus increasing the food value of the seed.

The present invention also provides a method for reducing the level of an endogenous protein in a seed by altering expression of a second protein in the seed that requires the same amino acid as the endogenous protein.

DETAILED DESCRIPTION OF THE INVENTION

As used herein, "genetically modified" means a plant cell stably incorporating a nucleic acid construct introduced by transformation methods. The term "wild type" refers to an untransformed plant cell.

The invention also embraces reducing translation of nucleic acid sequences encoding endogenous proteins. "Endogenous" protein refers to the native protein normally found in its natural location in the plant.

In addition, the invention comprises the methods of preparing and using the various DNA constructs of the present invention. Plants, seeds, and microorganisms transformed with the nucleic acid sequences described are also embodiments of the invention.

Preferred plants that produce seeds wherein protein content may be improved by this method include, but are not limited to, soybeans, canola, corn, sunflower, wheat, barley, oats, millet, rice, sorghum, and rye. The seeds may be used directly as feed or food, or further processing may occur. In the practice of the present invention, the most preferred plant seed is Glycine max, the preferred endogenous protein whose content is diminished is a protease inhibitor, and the preselected protein is a methionine-rich, seed storage protein.

In accordance with this invention, there is provided a simple, rapid, and reliable process for the production of transgenic soybean plants with reduced protease inhibitor activity in the resulting seeds. The method is genotype independent and shows a substantial improvement over previously-used systems because it eliminates or considerably reduces necessary, time-consuming, and costly steps to eliminate protease inhibitor activity from soy food products.

As used herein, "promoter" refers to a DNA sequence in a gene, usually upstream (5') to its coding sequence, which controls the expression of the coding sequence by providing the recognition for RNA polymerase and other factors required for promoter transcription. Preferred promoters are those that allow expression of the preselected protein specifically in seeds to avoid any potential deleterious effect in non-seed organs. Examples of seed-specific promoters include, but are not limited to, the promoters of seed storage proteins which express these proteins in seeds in a highly regulated manner. Thompson, et al. (1989) *BioEssays* 10, 108–113. Several seed specific promoters for expression of proteins in seeds of dicotyledonous plants that will be of particular use include bean β-phaseolin, globulin 1, napin, β-conglycinin, and soybean lectin. For monocotyledonous plants, maize 15 kD zein, 22 kD zein, γ-zein, waxy, shrunken 1, and shrunken 2 promoters will be particularly useful to produce expression of peptides. Those skilled in the art will recognize other promoters as well that will provide constructs for increased levels of the preselected protein in the plant chosen for transformation.

In a highly preferred embodiment, the preselected protein is a methionine-rich 2S seed storage protein such as Brazil nut protein (BNP). Altenbach, et al., (1987) *Plant Mol. Biol.*, 8, 239–250. A natural or constructed DNA or RNA sequence encoding this protein is introduced into plant cells by any method of transformation that stably incorporates the gene into the plant genome. This can include a variety of vectors, such as viral vectors, episomal vectors, shuttle vectors, Ti plasmid vectors and the like, all in accordance with well known procedures. Sun, et al., (1991) Eur. Patent Appl. EP No. 295,959. A "vector" is a replicon, such as a plasmid, cosmid, or bacteriophage, to which another DNA segment may be attached so as to bring about replication of the attached segment, or to allow its introduction into a cellular host.

As used herein with respect to a protein, the term "heterologous" means that the gene or gene fragment encoding the protein is obtained from one or more sources other than the genome of the species of plant within which it is ultimately expressed. The source can be natural, e.g., the gene can be obtained from another source of living matter, such as bacteria, yeast, fungi and the like, or a different species of plant. The source can also be synthetic, e.g., the gene or gene fragment can be prepared in vitro by chemical synthesis.

As used herein with respect to a preselected protein, the term "expresses" means that the gene encoding this protein is stably incorporated into the genome of the cells, so that the product encoded by the gene, e.g., a methionine-rich protein such as Brazil nut protein (BNP), is produced within the cells. For example, novel plants resulting from expression of BNP, contain extractable seed BNP levels of 0.5%, and preferably, at least 2%. Furthermore, as a result of BNP expression, the endogenous protein levels are diminished 5%, or preferably at least 50% or more. Those skilled in the art will recognize that the levels of extractable protein necessary to reduce endogenous protein levels may vary since different proteins will contain different levels of the desired amino acid residues.

Levels of an endogenous protein in a plant seed are reduced by the use of nucleic acid sequences inserted into the genome of a plant to cause the expression of a preselected protein, the sequence of which requires a limiting amino acid necessary to construct the primary structure of the endogenous protein. Synthesis of the preselected protein removes the source of the amino acid for synthesis of the endogenous protein, thus inhibiting its synthesis and subsequent presence in the seed. The amount of inhibition of the endogenous protein will depend on the location in the genome and the number of copies of the heterologous gene in the genetically-modified cell. These will affect expression of the preselected protein. Transgenic plants will exhibit a variety of different phenotypic expressions of the preselected protein, and selecting plants with high levels of expression can be readily achieved by skilled artisans in accordance with the present invention.

The properties of the nucleic acid sequences encoding the preselected protein may be varied and the preferred embodiment describes a number of features which may be advantageous but that a person skilled in the art will recognize as not being absolutely essential. These include the selection of a particular construct and vector to introduce the sequence into the cell and produce expression of the protein. A skilled artisan can construct an expression cassette adequate for expression of the preselected protein in the chosen cellular system with no undue experimentation. The heart of the invention is the level of expression of the preselected protein; therefore, additional copies of the nucleic acid sequence will normally result in increased inhibition of synthesis of the endogenous protein.

By way of example, and not limitation, those skilled in the art will readily appreciate that additional proteins may be substituted for the BNP protein as the preselected seed protein. The skilled artisan will recognize that choice of the preselected protein will be based on the amino acid composition of the protein and its ability to accumulate in seeds. This includes all classes of seed storage proteins; the 2S, 7S, and 11S proteins with or without modification to increase the content of the designated amino acid in the protein. The amino acid can be chosen for its nutritional value to produce a value-added trait to the plant as well as its purpose as a sink to limit availability to the designated endogenous protein. Examples of suitable sources for protein sequences usable in accordance with the present invention are plants, in particular higher plants. Amino acids desirable for value-added traits as well as a source to limit synthesis of an endogenous protein include, but are not limited to methionine, cysteine, glycine, lysine, tryptophan, and tyrosine.

As used herein, "plant" refers to either a whole plant, a plant part, a plant cell, or a group of plant cells. The class of plants which can be used in the method of the invention is generally as broad as the class of seed-bearing higher plants amenable to transformation techniques, including both monocotyledonous and dicotyledonous plants. The transformation of the plants in accordance with the invention may be carried out in essentially any of the various ways known to those skilled in the art of plant molecular biology. These include but are not limited to particle bombardment, microinjection, electroporation, and Agrobacterium-mediated DNA transfer.

Following transformation, regeneration will normally be involved in obtaining a whole plant from the transformation process. Techniques for regenerating plants from tissue culture, such as transformed protoplasts or callus cell lines, are known in the art. See, e.g., Phillips, et al (1981) *Plant Cell Tissue Organ Culture* 1, 123; Patterson, K. E. and N. P. Everett (1985) *Plant Sci.* 42, 125–132; Wright, et al. (1987) *Plant Cell Reports* 6, 83–89; Barwale, et al (1986) *Planta* 167,473. The selection of an appropriate method is within the skill of the art.

Examples of the practice of the present invention detailed herein relate specifically to soybean plants and expression vectors operable in dicots. Soybean was chosen as a model system for these examples primarily because of the present capability to regenerate soybean plants from transformed individual soybean cells in a manner now known in the art. The expression vectors utilized herein are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant calli and which express preselected seed proteins. For those species not presently regenerable, the present invention is fully operable when the techniques for such regeneration become developed.

In addition, chimeric expression vectors involving seed proteins are also known and have been described in the literature which have been demonstrated to be operable in cells of monocots, at least in tissue culture. It is reasonable then to expect that these vectors will also be operable in whole monocot plants when the techniques for regenerating these plants are perfected so that any preselected seed protein can be expressed in any monocotyledonous plant seed. The present invention is thus applicable to monocots as well as to dicots.

Therefore, practice of this invention can be used to improve crop plants like rice, maize, wheat, and barley with few modifications. An example of such an embodiment would be the introduction of a high lysine derivative of α-hordothionin into a barley or wheat cell to reduce the purothionin content of the seed and increase its lysine content.

Thionins are small antimicrobial proteins present in the endosperm of barley, wheat, and other plant species. Florack, et al. (1994) *Plant Mol. Biol.* 24, 83–96. Native α-hordothionin is rich in arginine and lysine residues, containing five residues (10%) of each. Several derivatives of this protein have been made in which other amino acids were replaced with lysine to produce a compound less toxic to fungi and significantly more enriched with lysine (29% lysine).

Purothionins are also small, lysine-rich proteins in the endosperm of wheat and several other species of Gramineae. Wada, K. (1982) *Plant & Cell Physiol.* 23(8), 1357–1361. Purothionins are lethal to brewer's yeast and, as a result, barley or wheat with high levels of these proteins cannot be used for making high quality beers.

However, according to this invention, a high-lysine α-hordothionin or another genetically-engineered thionin designed for lysine enrichment and reduced toxicity to microorganisms could be used to decrease the levels of purothionins and increase the lysine content of barley, wheat, or other graminaceous plants. The lysine-enriched residue could be sold for feed following the brewing process.

The foregoing is one description of the scope of the invention and a skilled artisan will recognize many other examples of plant improvement to which the invention can be applied.

The present invention can be better understood by reference to the following more detailed example which illustrates its various applications, but is in no way intended to limit the scope thereof.

EXPERIMENTAL

Transformation of Glycine max with a Methionine-rich Seed Storage Protein

Plant transformation

Soybean (Glycine max) seed, Pioneer variety 9341, was surface sterilized by exposure to chlorine gas evolved in a glass bell jar. Gas was produced by adding 3.5 ml hydrochloric acid (34–37% w/w) to 100 ml sodium hypochlorite (5.25% w/w). Exposure was for 16–20 hours in a container approximately one cubic foot in volume. Surface sterilized seed was stored in petri dishes at room temperature. Seed was germinated by plating on 1/10 strength agar solidified medium according to Gamborg [B5 basal medium with minimal organics, Sigma Chemical Co., cat. no. G5893, 0.32 gm/L; sucrose, 0.2% w/v and 2-[N-morpholino] ethanesulfonic acid (MES), 3.0 mM] without plant growth regulators and culturing at 28° C. with a 16 hour day length and cool white fluorescent illumination of approximately 20 mEm2S1. After three or four days, seed could be prepared for cocultivation. The seed coat was removed and the elongating radicle was removed 3–4 mm below the cotyledons. Ten prepared seeds were held in each of several petri dishes.

Construction of plasmids

For construction of the plasmid p12GUSBN17, containing one copy of the chimeric methionine-rich protein gene (BNP), we used the plasmid pARC12 (Prosen D. E. and R. B. Simpson (1987) *Biotechnology* 5, 966–971). This is a 29.5 kb plasmid which is part of a binary vector system of Agrobacterium and contains the chimeric gene nopaline synthase/neomycin phosphotransferase II as a selectable marker for plant cells. The chimeric gene, CaMV35S/β-glucuronidase, obtained from the plasmid pB1221 (Jefferson, R. A. (1987) Plant *Mol. Bio. Reporter* 5(4), 387–405) was inserted into pARC12, resulting in plasmid p12GUS-15. The plasmid pD3-8-12 (Altenbach, et al. (1989), *Plant Mol. Biol.* 13, 513–522), contains the BNP gene in the vector pTZ19U. The pD3-8-12 plasmid was cleaved with Hind III and inserted into the Hind III site of plasmid p12GUS-15. The resulting plasmid p12GUSBN17 is about 36 kb in size, contains one copy of the BNP gene, and confers resistance to ampicillin and tetracycline to the bacterial host.

For the construction of a plasmid containing four copies of the methionine-rich protein gene, the plasmid pD3-8-12 was used as the starting point. The BNP gene was excised from pD3-8-12 by digestion with Eco R1, Hind III, and Xmn 1. The ends of the fragment were made blunt with the Kenow fragment of DNA polymerase, and a 3 kb fragment containing the chimeric gene was gel-purified. This fragment was ligated to the plasmid pD3-8-12 which had been digested with Sma 1 and treated with calf intestinal phophatase. The resulting plasmid, called pD3-8-12-2X, contained two copies of the chimeric methionine-rich BNP gene in tandem array.

To produce the plasmid containing four copies of the chimeric gene, the pD3-8-12-2X plasmid was digested with Eco R1 and Hind III and the ends were made blunt with the Klenow fragment of DNA polymerase. A 6 kb fragment containing two copies of the chimeric gene was isolated. This fragment was ligated to the plasmid pD3-8-12-2X which had been digested with Sma I and treated with calf intestinal phosphatase. The resulting plasmid is pD3-8-12-4X.

The chimeric BNP genes were then inserted into the Ti plasmid vector pARC12. A 12 kb fragment from pD3-8-12-4X was excised by digestion with Eco R1 and Hind III and ligated to pARC12 which had been digested with Eco R1 and Hind III. The resulting plasmid, p12-4X, contains four copies of the BNP gene between the tDNA borders, as well as a chimeric nopaline synthase-neomycin phosphotransferase II gene for selection in plant cells. The plasmid was then transferred from *E coli* to *Agrobacterium tumefaciens* strain LBA 4404 by triparental mating. The identities of the resulting bacteria were confirmed by southern blot analysis. Preparation of *Agrobacterium tumefaciens* LBA4404/p12GUSBN17 and P12-4X Overnight cultures of *Agrobacterium tumefaciens* strain LBA 4404 harboring the binary plasmid p12GUSBN17 (DP1816, one copy BNP sequence) or p12-4X (DP1813, four copies BNP sequence), grown to log phase in Minimal A medium containing tetracycline, 1.0 mg/ml, were pooled and an optical density measurement at 550 nm was taken. Sufficient volume of the culture was placed in 15 ml conical centrifuge tubes such that upon sedimentation between 1.0 and $2.0 \times 10^{10}$ cells were collected in each tube, where O.D.550 $1.0=1.4 \times 10^9$ cells/ml. Sedimentation was by centrifugation at 6000 g for 10 minutes. After centrifugation the supernatant was decanted and the tubes were held at room temperature until inoculum was needed but not longer than one hour.

Transformation

Inoculations were conducted in batches such that each plate of seed was treated with a newly resuspended pellet of Agrobacterium. One at a time the pellets were resuspended in 20 ml inoculation medium. Inoculation medium consisted of B5 salts (G5893), 3.2 gm/L; sucrose, 2.0% w/v. 6-benzylaminopurine (BAP), 44 mM; indolebutyric acid (IBA), 0.5 mM; acetosyringone (AS), 100 mM and was buffered to pH 5.5 with MES, 10 mM. Resuspension was by vortexing. The inoculum was then poured into a petri dish containing prepared seed and the cotyledonary nodes were macerated with a surgical blade. This was accomplished by dividing seed in half by longitudinal section through the shoot apex preserving the two whole cotyledons. The two halves of the shoot apex were then broken off their respective cotyledons by prying them away with a surgical blade. The cotyledonary node was then macerated with the surgical blade by repeated scoring along the axis of symmetry. Care was taken not to cut entirely through the explant to the abaxial side. Twenty explants were prepared in roughly five minutes and then incubated for 30 minutes at room temperature without agitation. Additional plates were prepared during this time. After 30 minutes the explants were transferred to plates of the same medium solidified with Gelrite (Merck & Co., Inc.), 0.2% w/v. explants were embedded with the adaxial side up and level with the surface of the medium and cultured at 22° C. for three days under cool white fluorescent light, approximately 20 $mEm^2S^1$.

Culture and selection

After three days the explants were moved to liquid counterselection medium. Counterselection medium consisted of B5 salts (G5893), 3.2 gm/L; sucrose, 2.0% w/v; BAP, 5.0 mM ; IBA, 0.5 mM; vancomycin, 200 mg/ml; cefotaxime, 500 mg/ml and was buffered to pH 5.7 with MES, 3 mM. Ten explants were washed in each petri dish with constant, slow gyratory agitation at room temperature for four days. Counterselection medium was replaced four times.

The explants were then picked to agarose solidified selection medium. Selection medium consisted of B5 salts (G5893), 3.2 gm/L; sucrose, 2.0%, w/v; BAP, 5.0 mM; IBA, 0.5 mM; kanamycin sulfate, 50 mg/ml; vancomycin, 100 mg/ml; cefotaxime, 30 mg/ml; timentin, 30 mg/ml and was buffered to pH 5.7 with MES, 3.0 mM. Selection medium was solidified with SeaKem agarose, 0.3% w/v. The explants were embedded in the medium, adaxial side down and cultured at 28° C. with a 16 hour day length and cool white fluorescent illumination of 60–80 $mEm^2S^1$.

After two weeks explants were again washed with liquid medium on the gyrotory shaker. This time the wash was conducted overnight in counterselection medium containing kanamycin sulfate, 50 mg/ml. The following day explants were picked to agarose solidified selection medium. Again they were embedded in the medium, adaxial side down, Culture was as before for another two week period.

Regeneration

After one month on selective media transformed tissue became visible as green sectors of regenerating tissue against a background of bleached, less healthy tissue. Explants without green sectors were discarded, explants with green sectors were transferred to elongation medium. Elongation medium consisted of B5 salts (G5893), 3.2 gm/L; sucrose, 2.0% w/v; IBA, 3.3 mM; gibberellic acid, 1.7 mM; vancomycin, 100 mg/ml; cefotaxine, 30 mg/ml; and timentin, 30 mg/ml, buffered to pH 5.7 with MES, 3.0 mM. Elongation medium was solidified with gelrite, 0.2% w/v. They were embedded adaxial side up and cultured as before. Culture was continued on this medium with transfers to fresh plates every two weeks. When shoots became 0.5 cm in length they were excised at the base and placed in rooting medium in 13×100 mm test tubes. Rooting medium consisted of B5 salts (G5893), 3.2 gm/L; sucrose, 15 gm/L; nicotinic acid, 20 mM; pyroglutamic acid (PGA), 900 mg/L and IBA, 10 mM. It was buffered to pH 5.7 with MES, 3.0 mM and solidified with Gelrite, 0.2% w/v. After ten days the shoots were transferred to the same medium without IBA or PGA. Shoots were rooted and held in these tubes under the same environmental conditions as before.

When a root system was well established the plantlet was transferred to sterile soil mix in plant cons (ICN Biomedicals, Inc., cat. no. 26-720 & 1-02). Temperature, photoperiod and light intensity remained the same as before, Under these conditions the regenerants became vigorous, mostly normal (though small) plants. When their root systems again became well established a corner of the plant con was cut off and the plants were gradually hardened off in an environmental chamber or greenhouse. Finally they were potted in soil mix and grown to maturity, bearing seed, in a greenhouse.

Growth, increase, and harvest of transgenic soybeans

Seed from untransformed and transformed plants of the same variety (9341) was planted in the spring of 1992 and harvested in the fall of 1992 in Iowa. Each individual line was kept separate while grown in one or more 10.5 foot rows for maximum increase. This is the source of seed in Table 1 and the "JH2" source in Table 2. Lines from transformation events wherein one copy of the BNP gene was inserted are referred to as BNP1X. Lines in which four copies were inserted are designated BNP4X.

Most of the harvested BNP4X seed in the fall of 1992 was increased in Puerto Rico. This seed was planted by line in December, 1992 and harvested by line in March, 1993. This was source "PF2" in Table 2.

Part of the increased, harvested seed was returned for yield test and further laboratory testing. The rest was replanted by line in March, 1993 and harvested by line in June, 1993 in Puerto Rico. This was the source "PS3" in Table 2. The entire second cycle increase was about 2 acres, or a little more than 0.1 A per line.

Trypsin inhibitor analyses

Spectrophometric analysis of trypsin and chymotrypsin inhibitor activities in soybean seeds were carried out according to the published methods of Hymowitz, et al. (1992) *J. Agr. Food*, 40, 2356–2363. Analyses of trypsin inhibitor activity/gram (TIU/gram) and α-chymotrypsin inhibitor activity/gram (CIU/gram) are presented in Tables 1 and 2.

All samples submitted contained KTI. All samples contain the Ti-A allele. All samples contained BBI activity which was measured by two different methods: (1) trypsin inhibitor activity gel; and (2) α-chymotrypsin inhibitor activity gel. (BBI is a double-headed protease inhibitor, inhibiting both trypsin and α-chymotrypsin).

Table 1 shows the results of analysis of twelve soybean samples for trypsin and chymotrypsin inhibitor assay activity. All samples, except the normal controls, P9341, PR, were transformed to express higher levels of the amino acid methionine. This analysis included lines containing only one copy of the BNP gene: BX1P9341-1, BX1P9341-2, BX1P9341-3, BX1P9341-4, New 1X J2R17P23-24 and New 1X J2R17P18-20. Three replicates of 20 mg samples each representing five seeds selected at random from each of the 12 soybean samples were tested.

Except for two BNP1X samples, New 1X J2R17P23-24 and New 1X J2R17P18-20, all transgenic seed showed a reduction in both trypsin and α-chymotrypsin inhibitor activity compared to controls. In fact, α-chymotrypsin inhibitor activity was reduced tenfold in one sample of BNP4X and almost 60% in overall trypsin inhibitor activity.

The samples analyzed in Table 2 represent successive generations of three different BNP4X sources (PS2, PF2, JH2) of the same genetic lines. Seeds from JH2 were allowed to mature longer than seeds from designated sources PS2 and PF2.

Even more striking results are shown in Table 2. Compared to wild-type seed, the reduction in trypsin and α-chymotrypsin inhibitor activity is extraordinary, especially in the samples from the Iowa plots where the seeds had a longer maturation period.

TABLE 1

Spectrophotometric analysis of trypsin and chymotrypsin inhibitor activities in the seeds

| Sample | Repl. | A247/min | (TI) A247/min | TIU/gram | A256/min | (CI) A256/min | CIU/gram |
|---|---|---|---|---|---|---|---|
| BX1P9341-1 | 1 | 0.032 | 0.019 | 3518.52 | 0.018 | 0.007 | 54.46 |
| BX1P9341-1 | 2 | 0.034 | 0.017 | 3148.15 | 0.017 | 0.008 | 62.24 |
| BX1P9341-1 | 3 | 0.032 | 0.019 | 3518.52 | 0.017 | 0.008 | 62.24 |
| BX1P9341-2 | 1 | 0.032 | 0.019 | 3518.52 | 0.014 | 0.011 | 85.58 |
| BX1P9341-2 | 2 | 0.032 | 0.019 | 3518.52 | 0.015 | 0.01 | 77.80 |
| BX1P9341-2 | 3 | 0.033 | 0.018 | 3333.33 | 0.015 | 0.01 | 77.80 |
| BX1P9341-3 | 1 | 0.035 | 0.016 | 2962.96 | 0.017 | 0.008 | 62.24 |
| BX1P9341-3 | 2 | 0.035 | 0.016 | 2962.96 | 0.017 | 0.008 | 62.24 |
| BX1P9341-3 | 3 | 0.037 | 0.014 | 2592.59 | 0.017 | 0.008 | 62.24 |
| BX1P9341-4 | 1 | 0.038 | 0.013 | 2407.41 | 0.019 | 0.006 | 46.68 |
| BX1P9341-4 | 2 | 0.036 | 0.015 | 2777.78 | 0.017 | 0.008 | 62.24 |
| BX1P9341-4 | 3 | 0.037 | 0.014 | 2592.59 | 0.018 | 0.007 | 54.46 |
| P9341, PR | 1 | 0.027 | 0.024 | 4444.44 | 0.009 | 0.016 | 124.48 |
| P9341, PR | 2 | 0.03 | 0.021 | 3888.89 | 0.009 | 0.016 | 124.48 |
| P9341, PR | 3 | 0.028 | 0.023 | 4259.26 | 0.009 | 0.016 | 124.48 |
| NEW 1X J2R17P23-24 | 1 | 0.021 | 0.03 | 5555.56 | 0.008 | 0.017 | 132.26 |
| NEW 1X J2R17P23-24 | 2 | 0.022 | 0.029 | 5370.37 | 0.008 | 0.017 | 132.26 |
| NEW 1X J2R17P23-24 | 3 | 0.02 | 0.031 | 5740.74 | 0.008 | 0.017 | 132.26 |
| NEW 1X J2R17P18-20 | 1 | 0.021 | 0.03 | 5555.56 | 0.008 | 0.017 | 132.26 |
| NEW 1X J2R17P18-20 | 2 | 0.03 | 0.021 | 3888.89 | 0.011 | 0.014 | 108.92 |
| NEW 1X J2R17P18-20 | 3 | 0.027 | 0.024 | 4444.44 | 0.009 | 0.016 | 124.48 |
| BX4P9341-B3 | 1 | 0.041 | 0.01 | 1851.85 | 0.018 | 0.007 | 21.78 |
| BX4P9341-B3 | 2 | 0.041 | 0.01 | 1851.85 | 0.018 | 0.007 | 21.78 |
| BX4P9341-B3 | 3 | 0.04 | 0.011 | 2037.04 | 0.018 | 0.007 | 21.78 |
| BX4P9341-A6 | 1 | 0.04 | 0.011 | 2037.04 | 0.018 | 0.007 | 21.78 |
| BX4P9341-A6 | 2 | 0.04 | 0.011 | 2037.04 | 0.019 | 0.006 | 18.67 |
| BX4P9341-A6 | 3 | 0.04 | 0.011 | 2037.04 | 0.018 | 0.007 | 21.78 |
| BX4P9341-A4 | 1 | 0.037 | 0.014 | 2592.59 | 0.018 | 0.007 | 54.46 |
| BX4P9341-A4 | 2 | 0.036 | 0.015 | 2777.78 | 0.018 | 0.007 | 54.46 |
| BX4P9341-A4 | 3 | 0.036 | 0.015 | 2777.78 | 0.017 | 0.008 | 62.24 |
| BX4P9341-B6 | 1 | 0.042 | 0.009 | 1666.67 | 0.019 | 0.006 | 18.67 |
| BX4P9341-B6 | 2 | 0.043 | 0.008 | 1481.48 | 0.019 | 0.006 | 18.67 |
| BX4P9341-B6 | 3 | 0.04 | 0.011 | 2037.04 | 0.02 | 0.005 | 15.56 |
| BX4P9341-C5 | 1 | 0.042 | 0.009 | 1666.67 | 0.021 | 0.004 | 12.45 |
| BX4P9341-C5 | 2 | 0.043 | 0.008 | 1481.48 | 0.02 | 0.005 | 15.56 |
| BX4P9341-C5 | 3 | 0.044 | 0.007 | 1296.30 | 0.021 | 0.004 | 12.45 |

TABLE 2

Spectrophotometric analysis of trypsin (TIU) and chymotrypsin (CIU) inhibitor activities in the seeds

| STOCK NO. | SOURCE | A247/MIN | (TI) A247/MIN | TIU/GRAM | A256/MIN | (CI) A256/MIN | CIU/GRAM |
|---|---|---|---|---|---|---|---|
| P9341 | PF2 | 0.006 | 0.044 | 8148 | 0.004 | 0.018 | 140.04 |
| BX4P9341–9 | PF2 | 0.035 | 0.015 | 2778 | 0.017 | 0.005 | 15.56 |
| BX4P9341A4 | PF2 | 0.022 | 0.028 | 5185 | 0.011 | 0.011 | 34.23 |
| BX4P9341A6 | PF2 | 0.032 | 0.018 | 3333 | 0.017 | 0.005 | 15.56 |

TABLE 2-continued

Spectrophotometric analysis of trypsin (TIU) and chymotrypsin (CIU) inhibitor activities in the seeds

| STOCK NO. | SOURCE | A247/MIN | (TI) A247/MIN | TIU/GRAM | A256/MIN | (CI) A256/MIN | CIU/GRAM |
|---|---|---|---|---|---|---|---|
| BX4P9341A7 | PF2 | 0.036 | 0.014 | 2593 | 0.015 | 0.007 | 21.78 |
| BX4P9341B3 | PF2 | 0.034 | 0.016 | 2963 | 0.013 | 0.009 | 28.01 |
| BX4P9341B6 | PF2 | 0.035 | 0.015 | 2778 | 0.016 | 0.006 | 18.67 |
| BX4P9341C2 | PF2 | 0.033 | 0.017 | 3148 | 0.016 | 0.006 | 18.67 |
| BX4P9341C5 | PF2 | 0.034 | 0.016 | 2963 | 0.013 | 0.009 | 28.01 |
| BX4P9341C7 | PF2 | 0.025 | 0.025 | 4630 | 0.012 | 0.01 | 31.12 |
| P9341 | PS3 | 0.006 | 0.044 | 8148 | 0.005 | 0.017 | 132.26 |
| BX4P9341–9 | PS3 | 0.033 | 0.017 | 3148 | 0.014 | 0.008 | 24.90 |
| BX4P9341A4 | PS3 | 0.026 | 0.024 | 4444 | 0.013 | 0.009 | 28.01 |
| BX4P9341A6 | PS3 | 0.029 | 0.021 | 3889 | 0.013 | 0.009 | 28.01 |
| BX4P9341A7 | PS3 | 0.032 | 0.018 | 3333 | 0.015 | 0.007 | 21.78 |
| BX4P9341B3 | PS3 | 0.031 | 0.019 | 3519 | 0.014 | 0.008 | 24.90 |
| BX4P9341B6 | PS3 | 0.036 | 0.014 | 2593 | 0.017 | 0.005 | 15.56 |
| BX4P9341C2 | PS3 | 0.034 | 0.016 | 2963 | 0.014 | 0.008 | 24.90 |
| BX4P9341C5 | PS3 | 0.031 | 0.019 | 3519 | 0.013 | 0.009 | 28.01 |
| BX4P9341C7 | PS3 | 0.032 | 0.018 | 3333 | 0.014 | 0.008 | 24.90 |
| P9341 | JH2 | 0.009 | 0.041 | 7593 | 0.007 | 0.015 | 116.70 |
| BX4P9341–9 | JH2 | 0.039 | 0.011 | 2037 | 0.02 | 0.002 | 6.22 |
| BX4P9341A4 | JH2 | 0.039 | 0.011 | 2037 | 0.022 | 0 | <3.11 |
| BX4P9341A6 | JH2 | 0.035 | 0.015 | 2778 | 0.018 | 0.004 | 12.45 |
| BX4P9341A7 | JH2 | 0.035 | 0.015 | 2778 | 0.019 | 0.003 | 9.34 |
| BX4P9341B3 | JH2 | 0.035 | 0.015 | 2778 | 0.019 | 0.003 | 9.34 |
| BX4P9341B6 | JH2 | 0.034 | 0.016 | 2963 | 0.018 | 0.004 | 12.45 |
| BX4P9341C2 | JH2 | 0.038 | 0.012 | 2222 | 0.021 | 0.001 | 3.11 |
| BX4P9341C5 | JH2 | 0.037 | 0.013 | 2407 | 0.02 | 0.002 | 6.22 |
| BX4P9341C7 | JH2 | 0.038 | 0.012 | 2222 | 0.022 | 0 | <3.11 |

Amino acid analysis

The amino acid content of seeds from transformed and untransformed plants was analyzed by methods described in the *Official Methods of Analysis of the AOAC* (1990) Hilrich, K (ed.), AOAC International, Vol. 2, pp 1096–1097. The methionine content of transformed seed is shown in Tables 3 and 4 and is considerably increased compared to the untransformed seed. The relative content of all other amino acids measured remained the same in all samples.

TABLE 3

Amino Acid Analysis

| SOURCE | | ALAI | AGRI | ASPI | CYSI | GLUI | GLYI | HISI | ILEI | LEUI | LYSI | METI | PHEI | PRLI | SERI | THRI | TYRI | VALI |
|---|---|---|---|---|---|---|---|---|---|---|---|---|---|---|---|---|---|---|
| P9341 | PF2 | 1.38 | 2.64 | 3.25 | 0.48 | 4.61 | 1.19 | 1.07 | 1.74 | 2.35 | 2.29 | 0.51 | 2.06 | 2.06 | 1.59 | 1.54 | 1.86 | 1.63 |
| BX4P341–9 | PF2 | 1.74 | 3.28 | 4.25 | 0.69 | 6.55 | 1.42 | 1.06 | 1.76 | 2.92 | 2.36 | 0.82 | 1.94 | 2.46 | 1.69 | 1.47 | 1.44 | 1.76 |
| BX4P9341A4 | PF2 | 1.34 | 3.07 | 3.81 | 0.63 | 6.52 | 1.27 | 0.97 | 1.59 | 2.70 | 2.20 | 0.81 | 1.83 | 2.29 | 1.63 | 1.29 | 1.33 | 1.61 |
| BX4P9341A6 | PF2 | 1.31 | 3.04 | 3.77 | 0.60 | 6.56 | 1.26 | 0.96 | 1.58 | 2.69 | 2.16 | 0.81 | 1.82 | 2.32 | 1.65 | 1.27 | 1.32 | 1.60 |
| BX4P9341A7 | PF2 | 1.32 | 2.99 | 3.75 | 0.58 | 6.35 | 1.25 | 0.96 | 1.56 | 2.65 | 2.15 | 0.81 | 1.78 | 2.20 | 1.62 | 1.30 | 1.30 | 1.58 |
| BX4P9341B3 | PF2 | 1.49 | 2.92 | 3.75 | 0.58 | 6.36 | 1.33 | 0.96 | 1.54 | 2.61 | 2.17 | 0.70 | 1.77 | 2.30 | 1.67 | 1.31 | 1.30 | 1.56 |
| BX4P9341B6 | PF2 | 1.30 | 3.02 | 3.77 | 0.61 | 6.55 | 1.26 | 0.96 | 1.57 | 2.67 | 2.16 | 0.76 | 1.80 | 2.32 | 1.65 | 1.29 | 1.31 | 1.59 |
| BX4P9341C2 | PF2 | 1.28 | 3.36 | 3.74 | 0.60 | 6.46 | 1.24 | 0.94 | 1.54 | 2.64 | 2.12 | 0.84 | 1.77 | 2.26 | 1.62 | 1.29 | 1.30 | 1.55 |
| BX4P9341C5 | PF2 | 1.29 | 3.03 | 3.71 | 0.66 | 6.50 | 1.25 | 0.95 | 1.56 | 2.65 | 2.14 | 0.79 | 1.79 | 2.21 | 1.62 | 1.29 | 1.31 | 1.58 |
| BX4P9341C7 | PF2 | 1.27 | 3.28 | 3.67 | 0.53 | 6.36 | 1.24 | 0.93 | 1.52 | 2.60 | 2.10 | 0.83 | 1.74 | 2.26 | 1.60 | 1.28 | 1.28 | 1.53 |
| P9341 | PS3 | 1.34 | 3.07 | 3.99 | 0.60 | 6.48 | 1.31 | 0.94 | 1.66 | 2.68 | 2.31 | 0.57 | 1.83 | 2.31 | 1.68 | 1.38 | 1.32 | 1.64 |
| BX4P9341–9 | PS3 | 1.58 | 3.42 | 4.00 | 0.52 | 6.71 | 1.33 | 0.97 | 1.66 | 2.78 | 2.24 | 0.75 | 1.91 | 2.38 | 1.69 | 1.33 | 1.35 | 1.65 |
| BX4P9341A4 | PS3 | 1.53 | 3.40 | 3.91 | 0.51 | 6.66 | 1.30 | 0.96 | 1.62 | 2.75 | 2.20 | 0.78 | 1.87 | 2.37 | 1.67 | 1.29 | 1.33 | 1.61 |
| BX4P9341A6 | PS3 | 1.51 | 3.51 | 3.88 | 0.45 | 6.75 | 1.29 | 0.95 | 1.62 | 2.75 | 2.17 | 0.79 | 1.87 | 2.44 | 1.65 | 1.28 | 1.32 | 1.60 |
| BX4P9341A7 | PS3 | 1.60 | 3.57 | 3.95 | 0.50 | 6.34 | 1.30 | 0.97 | 1.65 | 2.77 | 2.15 | 0.78 | 1.86 | 2.36 | 1.56 | 1.31 | 1.19 | 1.63 |
| BX4P9341B3 | PS3 | 1.36 | 3.16 | 3.91 | 0.60 | 6.64 | 1.29 | 0.98 | 1.65 | 2.81 | 2.22 | 0.81 | 1.91 | 2.30 | 1.65 | 1.30 | 1.35 | 1.65 |
| BX4P9341B6 | PS3 | 1.50 | 3.46 | 3.88 | 0.53 | 6.68 | 1.28 | 0.97 | 1.61 | 2.76 | 2.14 | 0.77 | 1.89 | 2.32 | 1.66 | 1.27 | 1.35 | 1.60 |
| BX4P9341C2 | PS3 | 1.49 | 3.46 | 3.86 | 0.53 | 6.63 | 1.28 | 0.96 | 1.61 | 2.74 | 2.15 | 0.72 | 1.88 | 2.36 | 1.63 | 1.27 | 1.33 | 1.60 |
| BX4P9341C5 | PS3 | 1.58 | 3.67 | 3.95 | 0.49 | 6.22 | 1.29 | 0.97 | 1.66 | 2.79 | 2.14 | 0.78 | 1.87 | 2.28 | 1.55 | 1.29 | 1.36 | 1.64 |
| BX4P9341C7 | PS3 | 1.52 | 3.59 | 3.92 | 0.47 | 6.73 | 1.31 | 0.97 | 1.63 | 2.77 | 2.18 | 0.80 | 1.90 | 2.44 | 1.67 | 1.26 | 1.36 | 1.62 |

TABLE 4

Amino Acid Analysis

| Variable | N | NMISS | MAX | MIN | MEAN | SUM | STD | CV |
|---|---|---|---|---|---|---|---|---|
| SOURCE | 20 | 0 | | | | | | |
| ALAI | 20 | 0 | 1.74 | 1.27 | 1.44 | 28.71 | 0.133 | 9 |
| ARGI | 20 | 0 | 3.67 | 2.64 | 3.25 | 64.94 | 0.270 | 8 |
| ASPI | 20 | 0 | 4.25 | 3.25 | 3.84 | 76.72 | 0.191 | 5 |
| CYSI | 20 | 0 | 0.69 | 0.45 | 0.56 | 11.16 | 0.066 | 12 |
| GLUI | 20 | 0 | 6.75 | 4.61 | 6.43 | 128.66 | 0.454 | 7 |
| GLYI | 20 | 0 | 1.42 | 1.19 | 1.28 | 25.69 | 0.047 | 4 |
| HISI | 20 | 0 | 1.07 | 0.93 | 0.97 | 19.40 | 0.035 | 4 |
| ILEI | 20 | 0 | 1.76 | 1.52 | 1.62 | 32.33 | 0.063 | 4 |
| LEUI | 20 | 0 | 2.92 | 2.35 | 2.70 | 54.08 | 0.114 | 4 |
| LYSI | 20 | 0 | 2.36 | 2.10 | 2.19 | 43.75 | 0.067 | 3 |
| METI | 20 | 0 | 0.84 | 0.51 | 0.76 | 15.23 | 0.084 | 11 |
| PHEI | 20 | 0 | 2.06 | 1.74 | 1.85 | 37.09 | 0.074 | 4 |
| PRLI | 20 | 0 | 2.46 | 2.06 | 2.31 | 46.24 | 0.092 | 4 |
| SERI | 20 | 0 | 1.69 | 1.55 | 1.64 | 32.75 | 0.040 | 2 |
| THRI | 20 | 0 | 1.54 | 1.26 | 1.32 | 26.31 | 0.071 | 5 |
| TYRI | 20 | 0 | 1.86 | 1.19 | 1.35 | 27.01 | 0.128 | 10 |
| VALI | 20 | 0 | 1.76 | 1.53 | 1.61 | 32.23 | 0.048 | 3 |

Polypeptide synthesis during late seed development

Twelve seeds were selected from transgenic (BNP4X) plants and twelve from untransformed controls, both from full pods just prior to browning and desiccation (i.e., very late in seed development). The seeds were divided into halves wherein one cotyledon was cultured in media supplemented with methionine and the other was cultured in the same media without methionine. After six days of culture the cotyledons were washed in distilled water and lyophilized.

On a dry weight basis, methionine-fed controls gained 3% more dry weight than their counterparts cultured in media without methionine. Methionine-fed BNP cotyledons gained 34% more dry weight than their counterparts cultured in media without methionine, suggesting that late in development these beans can use methionine to produce BNP.

Coomassie blue-stained PAGE separations of the proteins showed an increase in BNP as a direct result of feeding. These gels also show that the band which is commonly assumed to be naturally-occurring, 2S seed storage protein, a methionine-rich protein that disappears when BNP is expressed in transgenic soybeans, is present when the transgenic beans are fed methionine, demonstrating that methionine source is limiting storage protein accumulation.

Following amino acid analysis, the methionine-fed BNP samples (BNP+) were found to have a 20% increase in methionine in protein compared to the BNP samples cultured without methionine (BNP−). (Table 5) The untransformed control samples incubated with methionine (Control+) had a 19% increase in methionine in protein compared to the untransformed controls incubated without methionine (Control−). (A comparison of BNP−/Control− and BNP+/Control+ demonstrates how much methionine in protein results from the synthesis of BNP. These figures suggest more than an additive effect indicating that BNP selectively pulls methionine out of the amino acid pool.)

Under methionine-limiting conditions (BNP−, Control−), the transformed seeds accumulate more methionine-containing protein than the controls. When cultured with methionine, the transformed seeds also accumulate more methionine-containing protein than the controls (BNP+, BNP−). All of these results indicate that methionine is more likely to be incorporated into BNP than other proteins such as protease inhibitors.

TABLE 5

| Sample | Met levels (weight %) |
|---|---|
| BNP+ | 1.21 |
| BNP− | 1.01 |
| Control+ | 0.88 |
| Control− | 0.74 |
| Control+/Control− | +19% |
| BNP+/BNP− | +20% |
| BNP−/Control− | +36% |
| BNP+/Control+ | +38% |

The cotyledons from each of the experimental groups were ground into meal, defatted, and analyzed for trypsin and chymotrypsin inhibitor activity as previously described. (Table 6). Three replicates of meal from each of the experimental groups were analyzed.

Transformed seeds supplemented with methionine (BNP+) demonstrate trypsin inhibitor activity levels equal to or higher than that of unsupplemented controls (Control−). The α-chymotrypsin inhibitor activity level of the BNP+ meal was as high as that of the controls cultured with methionine (Control+). From these results, it is clear that methionine is limiting to the synthesis of KTI and BBI protease inhibitors and the BNP protein is a sink for methionine that would have been used to synthesize these inhibitors.

TABLE 6

Spectrophotomeric Analysis of Trypsin (TIU) and Chymotrypsin (CIU) Inhibitor Activities in the Defatted Seed Meal

| Sample # | Replication | A247/min | (TI) A247/min | TIU/g seed meal | A256/min | (CI) A256/min | CIU/g seed meal |
|---|---|---|---|---|---|---|---|
| BNP + | A | 0.025 | 0.02 | 7407 | 0.006 | 0.015 | 311 |
| BNP + | B | 0.023 | 0.022 | 8148 | 0.006 | 0.015 | 311 |
| BNP + | C | 0.023 | 0.022 | 8148 | 0.006 | 0.015 | 311 |
| BNP − | A | 0.037 | 0.008 | 2963 | 0.019 | 0.002 | 41 |
| BNP − | B | 0.036 | 0.009 | 3333 | 0.018 | 0.003 | 62 |
| BNP − | C | 0.035 | 0.01 | 3704 | 0.019 | 0.002 | 41 |
| Control + | A | 0.014 | 0.031 | 11481 | 0.005 | 0.016 | 332 |
| Control + | B | 0.015 | 0.03 | 11111 | 0.006 | 0.015 | 311 |
| Control + | C | 0.016 | 0.029 | 10741 | 0.006 | 0.015 | 311 |
| Control − | A | 0.023 | 0.022 | 8148 | 0.01 | 0.011 | 228 |
| Control − | B | 0.024 | 0.021 | 7778 | 0.01 | 0.011 | 228 |
| Control − | C | 0.024 | 0.021 | 7778 | 0.01 | 0.011 | 228 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Variations on the above embodiments are within the ability of one of ordinary skill in the art, and such variations do not depart from the scope of the present invention as described in the following claims.

We claim:

1. A plant seed that is genetically modified to preferentially express a preselected protein, whereby the content of an endogenous protein is diminished in the seed,
    wherein the preselected protein is a protein which accumulates in the seed,
    wherein the preselected protein requires a limiting amino acid necessary to produce the primary construct of the endogenous protein,
    wherein the endogenous protein is an antinutritional protein, and
    wherein the plant seed is soybean, canola, corn, sunflower, wheat, barley, oats, millet, rice, sorghum or rye.

2. A plant seed according to claim 1, wherein said preselected protein is a second endogenous protein which said seed is genetically modified to overexpress.

3. A plant seed according to claim 1, wherein said preselected protein is a heterologous protein that said seed is genetically modified to express.

4. A plant seed according to claim 1, wherein said species is soybean.

5. A plant seed according to claim 1, wherein said endogenous protein is a protease inhibitor.

6. A plant seed according to claim 5, wherein the protease inhibitor is a chymotrypsin or trypsin inhibitor.

7. A plant seed according to claim 1, wherein the amino acid is methionine, glycine, lysine, cysteine, tryptophan or tyrosine.

8. A plant seed according to claim 7, wherein the amino acid is methionine.

9. A plant seed according to claim 8, wherein the preselected protein is a storage protein.

10. A plant seed according to claim 9, wherein the preselected protein is a 2S protein.

11. A plant seed according to claim 7 wherein the preselected protein is an α-hordothionin or a derivative thereof.

12. A plant seed according to claim 1, wherein the preselected protein contains at least 10 percent lysine.

13. A method of reducing the level of an endogenous protein in a plant seed comprising transforming a plant to express a preselected protein in the seed at a level sufficient to inhibit the synthesis of the endogenous protein,
    wherein the preselected protein is a protein which accumulates in the seed,
    wherein the preselected protein requires a limiting amino acid necessary to produce the primary construct of the endogenous protein,
    wherein the endogenous protein is an antinutritional protein, and
    wherein the plant seed is soybean, canola, corn, sunflower, wheat, barley, oats, millet, rice, sorghum or rye.

14. A method according to claim 13 wherein the endogenous protein levels are diminished at least 5%.

15. A method according to claim 14 wherein the endogenous protein levels are diminished at least 50%.

* * * * *

(12) REEXAMINATION CERTIFICATE (4253rd)

United States Patent
Beach et al.

(10) Number: US 5,850,024 C1
(45) Certificate Issued: Jan. 9, 2001

(54) REDUCTION OF ENDOGENOUS SEED PROTEIN LEVELS IN PLANTS

(75) Inventors: Larry Beach, Des Moines; Bruce Orman, Ankeny; Jeff Townsend, West Des Moines; Laurie Thomas, Des Moines, all of IA (US)

(73) Assignee: Pioneer Hi-Bred International, Des Moines, IA (US)

Reexamination Request:
No. 90/005,232, Jan. 25, 1999

Reexamination Certificate for:
Patent No.: 5,850,024
Issued: Dec. 15, 1998
Appl. No.: 08/724,030
Filed: Sep. 23, 1996

Related U.S. Application Data

(63) Continuation of application No. 08/521,229, filed on Aug. 30, 1995, now abandoned, which is a continuation of application No. 08/390,398, filed on Feb. 16, 1995, now abandoned, which is a continuation of application No. 08/222,148, filed on Apr. 4, 1994, now abandoned.

(51) Int. Cl.$^7$ ............... A01H 5/10; A01H 5/00; C07K 14/415; C12N 5/14
(52) U.S. Cl. .............. 800/250; 800/322; 800/320.3; 800/320; 435/69.1; 435/430
(58) Field of Search ................ 800/298, 322, 800/320.3, 320; 435/69.1, 430

(56) References Cited

U.S. PATENT DOCUMENTS 5,811,654  9/1998  Janyes et al. .................. 800/205

FOREIGN PATENT DOCUMENTS

| 0 318 341 | 5/1989 | (EP) | C12N/15/00 |
| WO 91/13993 | 9/1991 | (WO) | C12N/15/82 |
| WO 92/14822 | 9/1992 | (WO) | C12N/15/29 |
| WO 93/03160 | 2/1993 | (WO) | C12N/15/82 |

OTHER PUBLICATIONS

Rice, J.A. et al., "Expression of Synthetic High Lysine in Mature Seeds of Transgenic Crop Plants", *J. Cell Biochem. Suppl. 18A*, p. 107, 1994.

Falco, S.C. et al., "Transgenic Crops with Improved Amino Acid Composition", *J. Cell Biochem Suppl. 18A*, p. 79, 1994.

Beach, L.R. et al., "Enhancing the Nutritional Value of Seed Crops", *Current Top Plant Physiol.*, vol. 7, pp. 229–238, 1992.

*Primary Examiner*—Elizabeth C. Kemmerer

(57) ABSTRACT

A plant seed and method of producing the same, genetically modified to express a preselected protein, the expression of which reduces the level of an endogenous protein in the seed. In particular, expression of a sulfur-rich, seed storage protein reduces the level of protease inhibitors in seeds.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–15 is confirmed.

* * * * *